United States Patent [19]
Nellemann et al.

[11] Patent Number: 5,602,395
[45] Date of Patent: Feb. 11, 1997

[54] GAMMA CAMERA HAVING PARTIAL SEPTAS AND MOVING SEPTAS FOR POSITRON EMISSION TOMOGRAPHY (PET)

[75] Inventors: Peter Nellemann, Pleasanton; Horace H. Hines, San Jose, all of Calif.; Gerd Muehllehner, Wayne, Pa.; Matthew J. Murphy, Los Altos, Calif.

[73] Assignee: ADAC Laboratories, Milpitas, Calif.

[21] Appl. No.: 537,008

[22] Filed: Oct. 2, 1995

[51] Int. Cl.⁶ .................................................. G01T 1/166
[52] U.S. Cl. ................. 250/363.03; 250/363.04; 250/363.1
[58] Field of Search ................. 250/363.03, 363.1, 250/363.04; 378/155

[56] References Cited

U.S. PATENT DOCUMENTS

| | | | |
|---|---|---|---|
| 1,874,577 | 8/1932 | Morrison | 378/155 |
| 2,767,323 | 10/1956 | Stara et al. | 378/155 |
| 3,955,088 | 5/1976 | Muehllehner | 250/363.03 |
| 4,150,292 | 4/1979 | Ter-Pogossian | 250/363.03 |
| 5,151,599 | 9/1992 | Monnet et al. | 250/363.03 |
| 5,210,420 | 5/1993 | Hartz et al. | 250/363.03 |
| 5,224,037 | 6/1993 | Jones et al. | 364/413.19 |
| 5,291,021 | 3/1994 | Tanaka et al. | 250/363.03 |
| 5,451,789 | 9/1995 | Wong et al. | 250/363.03 |
| 5,512,754 | 4/1996 | Enos | 250/363.1 |

FOREIGN PATENT DOCUMENTS

| | | | |
|---|---|---|---|
| 214288 | 10/1985 | Japan | 250/363.1 |
| 3115989 | 5/1991 | Japan | 250/363.1 |

OTHER PUBLICATIONS

David Rollo, *Nuclear Medicine Physics Instrumentation and Agents*, Mosby, St. Louis, (1977), pp. 295–303 no month.

C. J. Thompson, . . . , *The Effect of Collimation on Singles Rates in Multi–Slice PET*, IEEE Transactions on Nuclear Science, vol. 36, No. 1, Feb., 1989, pp. 1072–1077.

Siemens Product Brochure, *Three–Dimensional Positron Emission Tomography (PET) ECAT Scanner*, pp. 1–18, no date.

Dr. Everett W. Stoub, Ph.D., *ECAT Scanners Technical Introduction*, May, 1987, pp. 1–12, Siemens Gammasonics Inc., Des Plaines, Illinois.

*Primary Examiner*—Carolyn E. Fields
*Attorney, Agent, or Firm*—Blakely, Sokoloff, Taylor & Zafman LLP

[57] ABSTRACT

A gamma camera for a Positron Emission Tomography (PET) system comprises a single, continuous scintillation crystal having an imaging surface, and a first layer of septa disposed along the imaging surface between the object and the imaging surface. A gap is provided between the imaging surface and the first layer of septa to allow non stray radiation to reach the imaging surface. The septa may be arranged to have a long axis disposed at an acute angle away from perpendicular to an axis of rotation or made to move in relation to the imaging surface of the scintillation crystal to reduce cold spots on the image. Multiple layers of septa may be provided.

36 Claims, 14 Drawing Sheets

GAMMA CAMERA HAVING PARTIAL SEPTAS AND MOVING SEPTAS FOR POSITRON EMISSION TOMOGRAPHY (PET)

FIELD OF THE INVENTION

The present invention relates to the field of nuclear medicine systems. Specifically, the present invention relates to stray radiation shields in Positron Emission Tomography (PET) systems.

BACKGROUND

PET systems are used for imaging patients who have received doses of a radiopharmaceutical containing a positron-emitting substance. When a positron from the radiopharmaceutical is captured by an electron, two gamma rays are emitted at 180 degrees from each other. PET systems attempt to reconstruct image information by detecting these gamma rays and storing their coordinates. Multiple detectors are used to detect the two gamma rays in coincidence (in different detectors). Accordingly, PET systems use gamma ray detectors coupled in a coincidence detection mode.

A PET system employing two scintillation detectors is described in a paper presented by Gerd Muehllehner, M. P. Buchin, and J. H. Dudek entitled "Performance Parameters of a Positron Imaging Camera," published in the IEEE Transactions on Nuclear Science, Volume NS-23, No. 1, on February 1976 and also in a paper entitled "Performance Parameters of a Longitudinal Tomographic Positron Imaging System" by Paans, deGraaf, Welleweerd, Vaalburg and Woldring, in Nuclear Instruments and Methods, Volume 192, Nos. 2, 3, on Feb. 1, 1982 pages 491–500. A predecessor of PET systems known as Single Photon Emission Computed Tomography (SPECT) was proposed and developed by Anger in the 1950s.

A problem encountered by PET systems is the unnecessary detection of stray radiation. Radiation may enter the detector from directly under the detector or from outside the area directly under the detector. The area directly under the detector's imaging surface is the field of view, and radiation that comes from outside the field of view is known as stray radiation. Detecting this unnecessary stray radiation results in decreased efficiency of a detector by increasing the detector's count rate while not adding any image information. With an increased count rate, the detector electronics must spend more time counting to form a sufficiently precise image. Thus, the stray radiation increases the detector's dead time.

Figure 1:
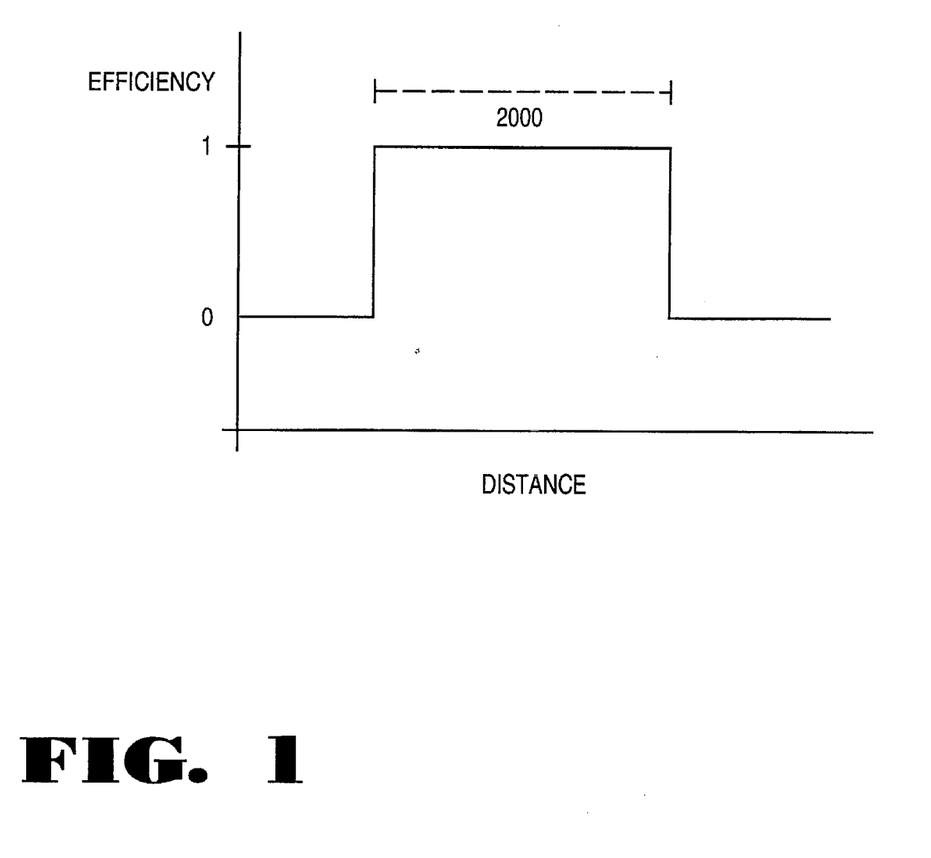
FIG. 1 illustrates an ideal efficiency curve.

The efficiency of a single detector may be represented by the ratio $R_N/R_S$, where $R_N$ represents the non stray count rate and $R_S$ represents the stray count rate. A higher value of $R_N/R_S$ indicates an increased efficiency because of the increase of the non stray count relative to the stray count for the single detector. Ideally, this ratio would be equal to one (100%) through the detector's field of view. In other words, ideally 100% of the radiation detected within the field of view would be non stray radiation. FIG. 1 shows an ideal efficiency curve.

Achieving even a relatively high ratio in actual practice, however, is problematic. The dosage of radiopharmaceutical can be increased so that $R_N$, the amount of non stray radiation, increases. With an increased $R_N/R_S$ ratio, however, the increase in stray radiation would not be as high as in a system with a lower $R_N/R_S$ ratio, even though the total amount of radiation has increased. In this manner, the imaging could be improved by the higher amount of non stray radiation without as large an increase in stray radiation and the corresponding detector dead time.

In some PET systems having gamma cameras with multiple discrete detectors (i.e., scintillation crystals), septa have been used to assign gamma rays to particular detectors of a gamma camera. Septa are plates made of a material tending to block gamma rays and are designed to block rays coming from certain angles relative to an imaging surface of the detector. Septa in existing systems start at the imaging crystal of the detector and emanate away from the crystal. Septa can potentially cause degradation of parts of the image, however. In particular, parts of the image may be degraded corresponding to parts of the detectors where the septum is placed. For example, in FIG. 3 ray 220 (non stray) is blocked, even though it is within the field of view. It would be advantageous to mitigate cold spots so as to improve image quality.

Hence, it is desirable to improve the efficiency of a gamma camera by reducing the amount of stray radiation detected relative to the amount of non-stray radiation detected. It is further desirable that such efficiency be improved while reducing the occurrence of cold spots.

SUMMARY AND OBJECTS OF THE INVENTION

An object of the invention is to improve image quality of a PET system.

Another object of the invention is to provide improved single detector efficiency in a PET scanner.

Another object of the invention is to increase the ratio of non-stray radiation to stray radiation detected in a single detector.

Yet another object of the present invention is to increase detection of coincidence gamma rays without a corresponding increase in stray radiation detection.

Another object of the invention is to help reduce cold spots that may be formed when detectors are rotated about the patient.

These and other objects are provided for in a gamma camera comprising a detector having a single, continuous scintillator which has an imaging surface, and a first layer of septa. The septa are disposed along the imaging surface between the object and the imaging surface. The septa are for blocking stray radiation from outside a field of view of the detector. A specific embodiment of the gamma camera further comprises a gap between the imaging surface and the first layer of septa for allowing non stray radiation to reach the scintillator. In another embodiment, the detector has moving septa.

Other objects, features, and advantages of the present invention will be apparent from the accompanying drawings and from the detailed description which follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 2:
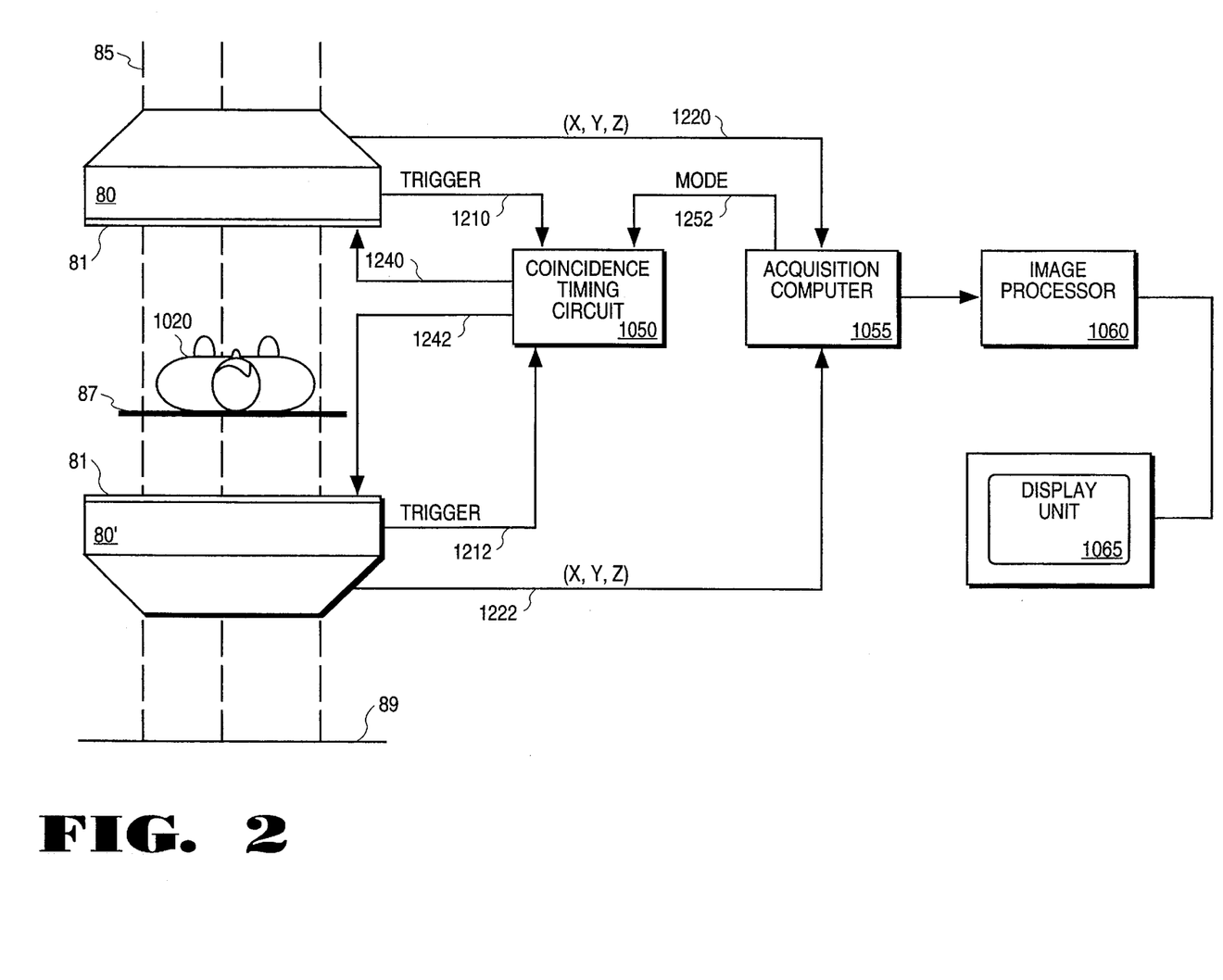
FIG. 2 illustrates a block diagram of a dual head gamma camera system.

The various embodiments of the present invention described herein are used in conjunction with a dual head scintillation detector camera system. Alternative embodiments of the present invention can be used within a camera system having more than two detector heads. Referring to FIG. 2, a high level diagram of a dual head detector gamma camera system of the present invention is shown. Generally, the system of the present invention includes a pair of gamma camera detectors 80 and 80' ("dual head") composed of a plurality of photomultiplier tubes, PMTs, arranged in a two dimensional matrix and optically coupled to a glass plate to receive light (e.g., visible photons) from a scintillation crystal 81. The PMT array constitutes a photodetector. The scintillation crystal 81 can be composed of thalium-activated sodium iodine, NaI(Tl). The detector pair are shown disposed opposite each other in a 180 degree configuration.

Gamma rays that strike the scintillation crystal 81 cause scintillation events that release a number of visible light photons that are detected by the PMTs with different light intensities. Each PMT reports in the form of an analog signal indicative of the amount of light energy detected as a result of the scintillation event. In one embodiment, these signals are digitized at an early circuit stage and are processed digitally. The gamma camera detectors 80 and 80' are of the Anger type and can be of a number of well known and commercially available designs. An exemplary gamma camera detector used by one embodiment can contain as many as 55 or 108 PMTs. A detector of the pair can also use smaller diameter PMTs along the edges to increase the detector's field of view. An embodiment of the present invention uses forty-nine 76 mm round PMTs and six 51 mm round PMTs for edge filling, however; the number of PMTs, their sizes and their configurations can be varied.

The detectors 80 and 80' are similarly constructed, such that discussions with respect to one detector are applicable to both. The detector pair 80 and 80' are mounted on a gantry 85 which can rotate the detectors 80 and 80' in various orbits (ECT projections) around an object (e.g., a patient) 1020 resting on table 87 (e.g., for ECT scanning operations), thus forming an axis of rotation 1530. The detector pair can rotate about a center of rotation through a number of projection angles, as is known in gamma camera technology. The gantry 85 and table 87 rest on base 89. The detector pair 80 and 80' can also be directed transversely across the table 87 (e.g., for total body scanning operations) or placed over the patient 1020 for static imaging.

Upon an event detection in either detector 80 or 80', signals 1210 and 1212, respectively, carry initial event detection trigger pulses to a programmable coincidence timing circuit 1050 (CTC). The CTC unit 1050 then generates valid event trigger signals over lines 1240 and 1242, respectively, back to the detectors for the 80 and 80'. The valid event trigger signals 1240 and 1242 are used by the detectors to start (or reset) their accumulators (integrators) which accumulate (integrate) the energy of the detected scintillation and are therefore called "valid event" trigger signals. Integration is not started until a coincidence is detected between detector 80 and 80'. After integration and centroiding, the detectors 80 and 80' output an X, Y, and Z value over lines 1220 and 1222, respectively. These signals indicate the coordinate value (X, Y) ("localization") of the detected event with respect to the detector and its measured energy value, Z. Within embodiments that use more than two detector heads, event detection information from each detector head is forwarded to the CTC unit 1050 that then detects coincidence between any two detectors feeding the CTC event detection information.

Hardware is included within each detector for digitizing the PMT channel signals, correcting these signals, and outputting X, Y, and Z values. To this extent, each detector 80 and 80' contains preamplification and digitization hardware as well as a Digital Event Processor. This hardware can be located within or outside the scintillation detectors 80 and 80'.

The values transmitted over bus 1220 and bus 1222 are input to an acquisition computer system 1055. The acquisition computer 1055 stores the values for each detected event for each projection angle and this information is routed to an image processor 1060 which contains a standard user interface. In the image processor 1060, events associated with various ECT projection angles are stored in the memory of the computer system in order to generate image information and form count density information. This image information is collected in the form of a matrices for the different ECT projection angles. Image matrices are generally collected at different ECT angles and then a reconstruction is done, using tomographic reconstruction to generate a three-dimensional image ("reconstruction") of an organ. The image processor 1060 also performs image reconstruction, non uniform attenuation correction and uniformity correction based on the acquired event data. The image processor 1060 is also coupled to a display unit 1065 (which can include a hardcopy device) for visualizing images captured by the camera system. This circuitry can alternatively be located outside the detector heads 80 and 80' or partially spread inside and partially outside of the detector heads 80 and 80'.

Figure 3:
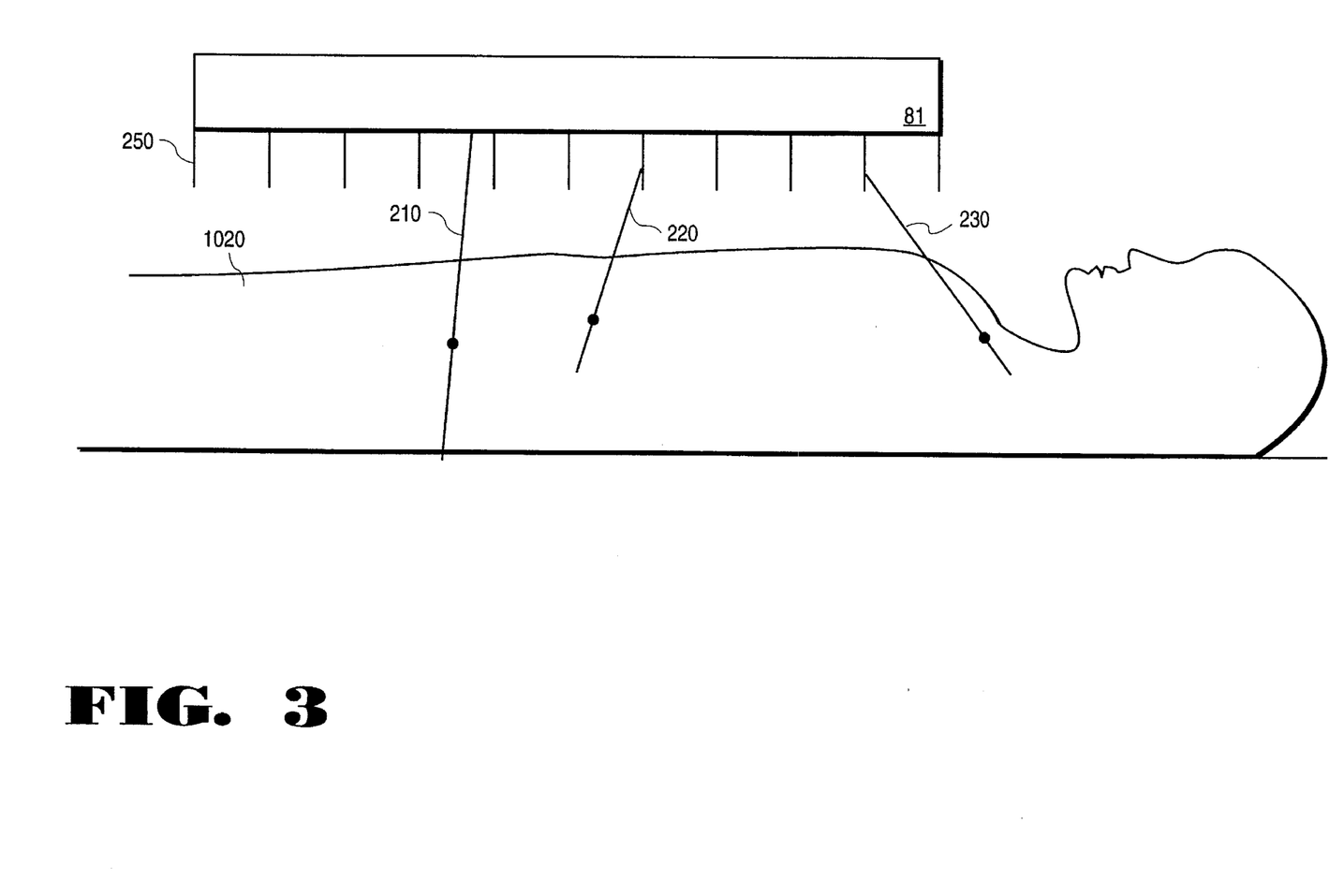
FIG. 3 illustrates septa in a gamma camera imaging system.

Embodiments of the present invention may be used in various gamma camera systems. In the present invention, septa are implemented in conjunction with a continuous-detector gamma camera in order to improve the efficiency of the gamma camera. Referring to FIG. 3, a schematic view of a gamma camera having a single, continuous scintillation crystal 81 and septa 250 is shown. The septa 250 tend to block stray radiation from outside the field of view. For example, ray 230 (stray) is blocked by the septa while ray 210 (non stray) is detected. However, the septa 250 also block some non-stray (desirable) radiation, as illustrated by ray 220.

Figure 4:
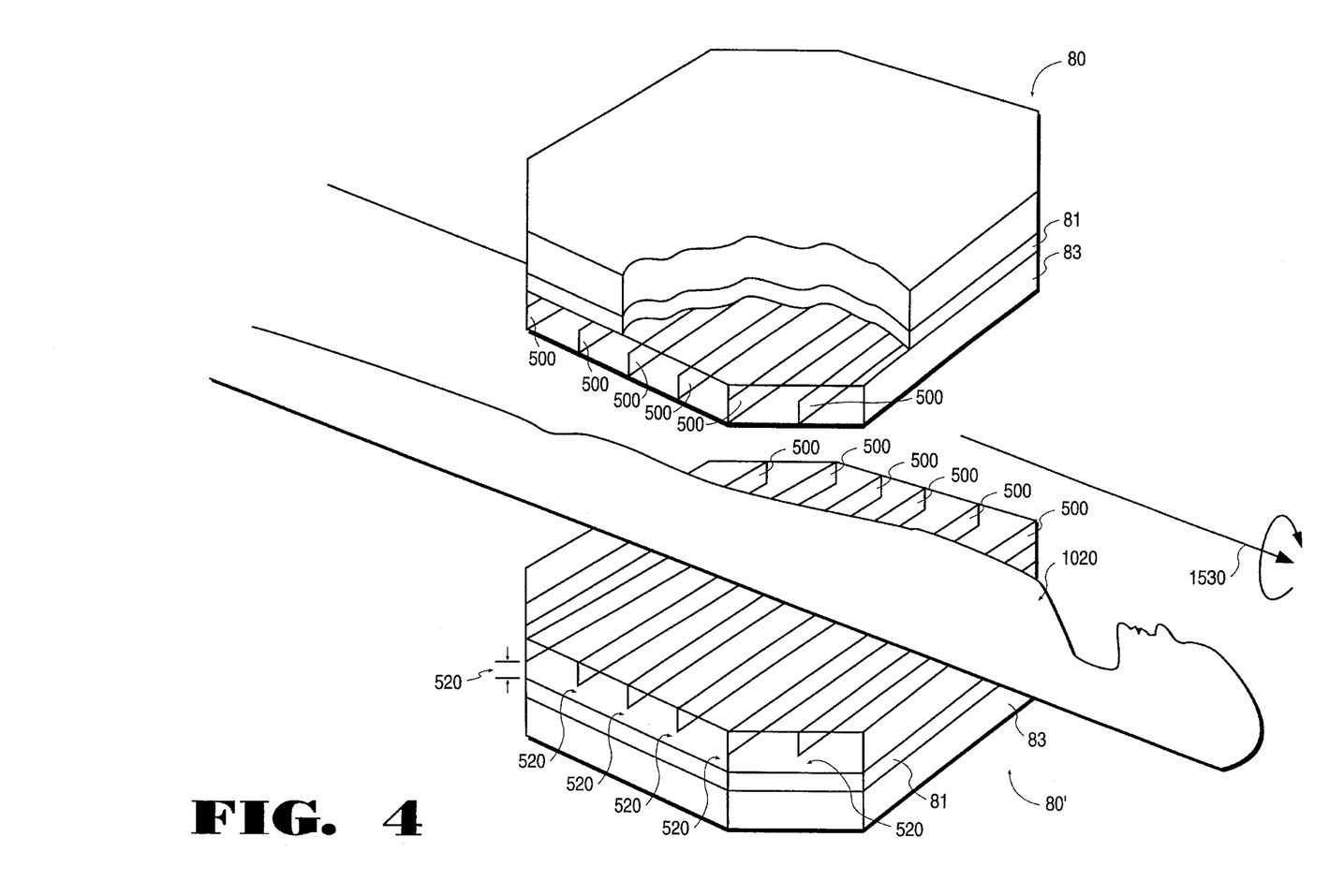
FIG. 4 illustrates detectors with septa and a patient.
Figure 5A:
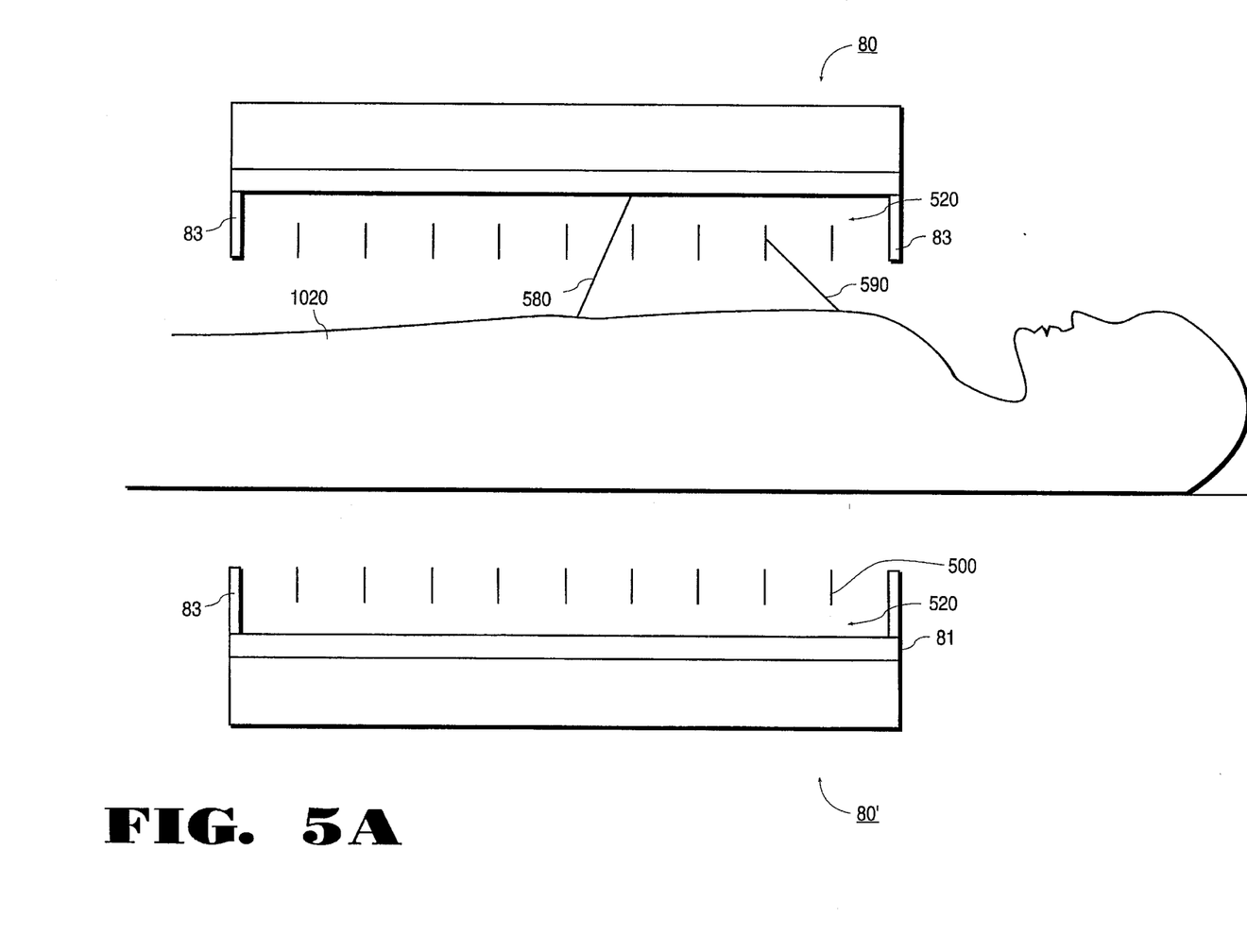
FIG. 5A illustrates detectors with septa.

FIG. 4 illustrates another embodiment, in which a detector 80 comprises a single, continuous scintillation crystal 81. The detector 80 also comprises a first layer of septa, including a number of individual septa 500 disposed along the imaging surface of the crystal 81 between the object 1020 and the imaging surface. In the embodiment of FIG. 4, the septa 500 run substantially perpendicular to the axis of rotation 1530 of the detectors. In addition, there is a gap 520 between the septa 500 and the imaging surface, as shown in FIG. 5A. The gap 520 allows desirable non stray radiation to pass under the septa 500 to the imaging surface, while stray radiation 590 is blocked by the septa 500. It should be noted, however, that the gap 520 is not required in order to use septa in accordance with the present invention.

Each of the septa 500 is substantially rectangular in shape, and the short axis 1560 of the septum 500 is substantially perpendicular to the imaging surface of the crystal 81. For improved performance the short axis 1560 of the septa 500 may be positioned somewhat off from perpendicular to the imaging surface. The septa 500 have a thickness of approximately 5 mm.

Figure 5B:
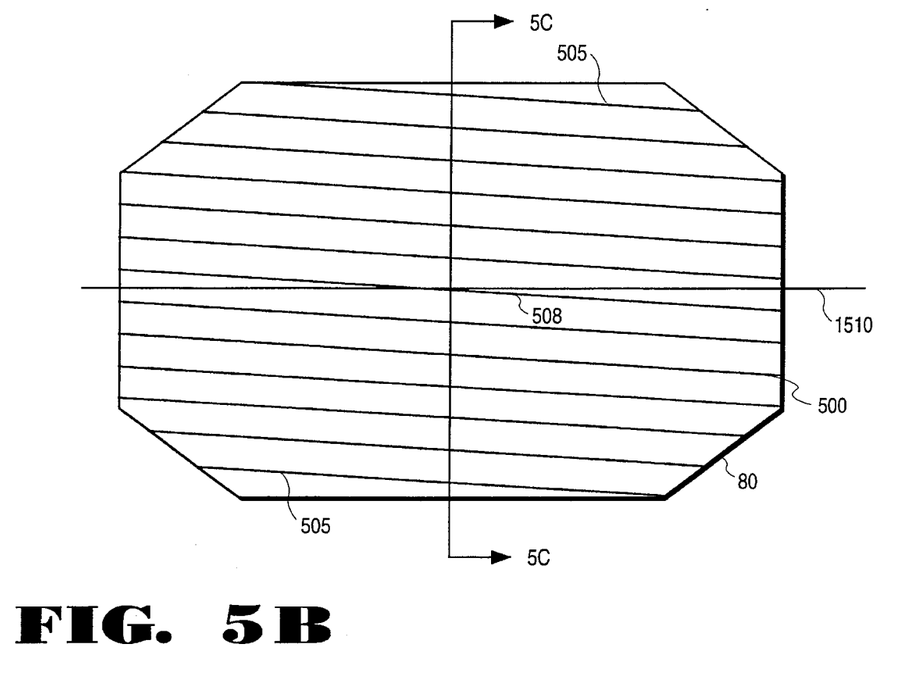
FIG. 5B illustrates a top view of a gamma camera detector having septa.
Figure 5C:
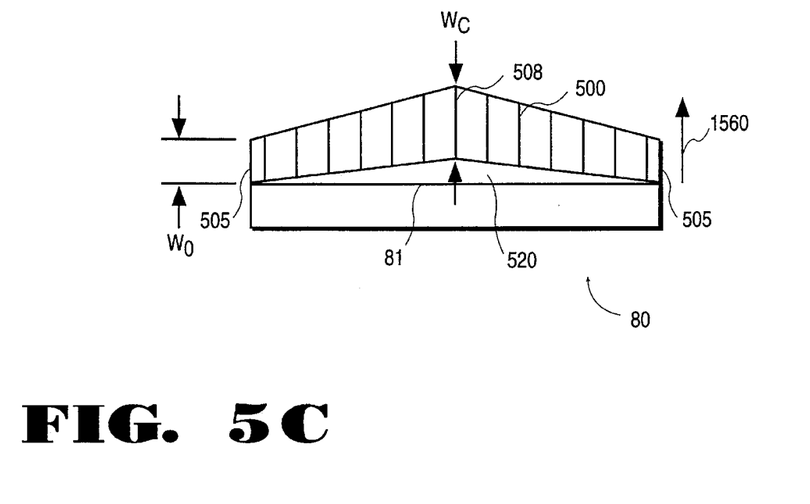
FIG. 5C illustrates a cross-sectional view of a gamma camera detector with septa of unequal widths.

The present invention may be implemented such that the septa 500 of a given detector 80 do not have equal width (width is the dimension measured in the direction of the short axis 1560) in order to allow more non-stray radiation to reach the crystal. Referring to FIGS. 5B and 5C, the present invention may be implemented such that the width of a given septum depends upon the location of that septum along the imaging surface. In the embodiment shown in FIGS. 5B and 5C, the outermost septa 505 of the detector 80 have a width $W_o$ of approximately 0.5 inches, while the center septum 508 (the septum closest to the center axis 1510) has a width $W_c$ of approximately 1.6 inches. Septa located between the outermost septa 505 and the center septa 508 have different widths ranging between $W_o$ and $W_c$. Because there is relatively little stray radiation near the edges of the detector 80, this construction may be used to allow more non-stray radiation to reach the crystal than if all septa had widths equal to that of the center septum 508, without significant increasing the stray radiation reaching the crystal.

Moreover, the present invention may be implemented such that the size of the gap 520 between a given septum and the imaging surface depends upon the location of that septum along the imaging surface. Referring again to FIG. 5C, there is no gap between the outermost septa 505 and the imaging surface, while there is a gap 520 between each of the other septa and the imaging surface. The size of the gap 520 increases for septa closer to the center axis 1510 of the detector, such that the gap 520 is largest at approximately 0.8 inches between the center septum 508 and the imaging surface.

Figure 5D:
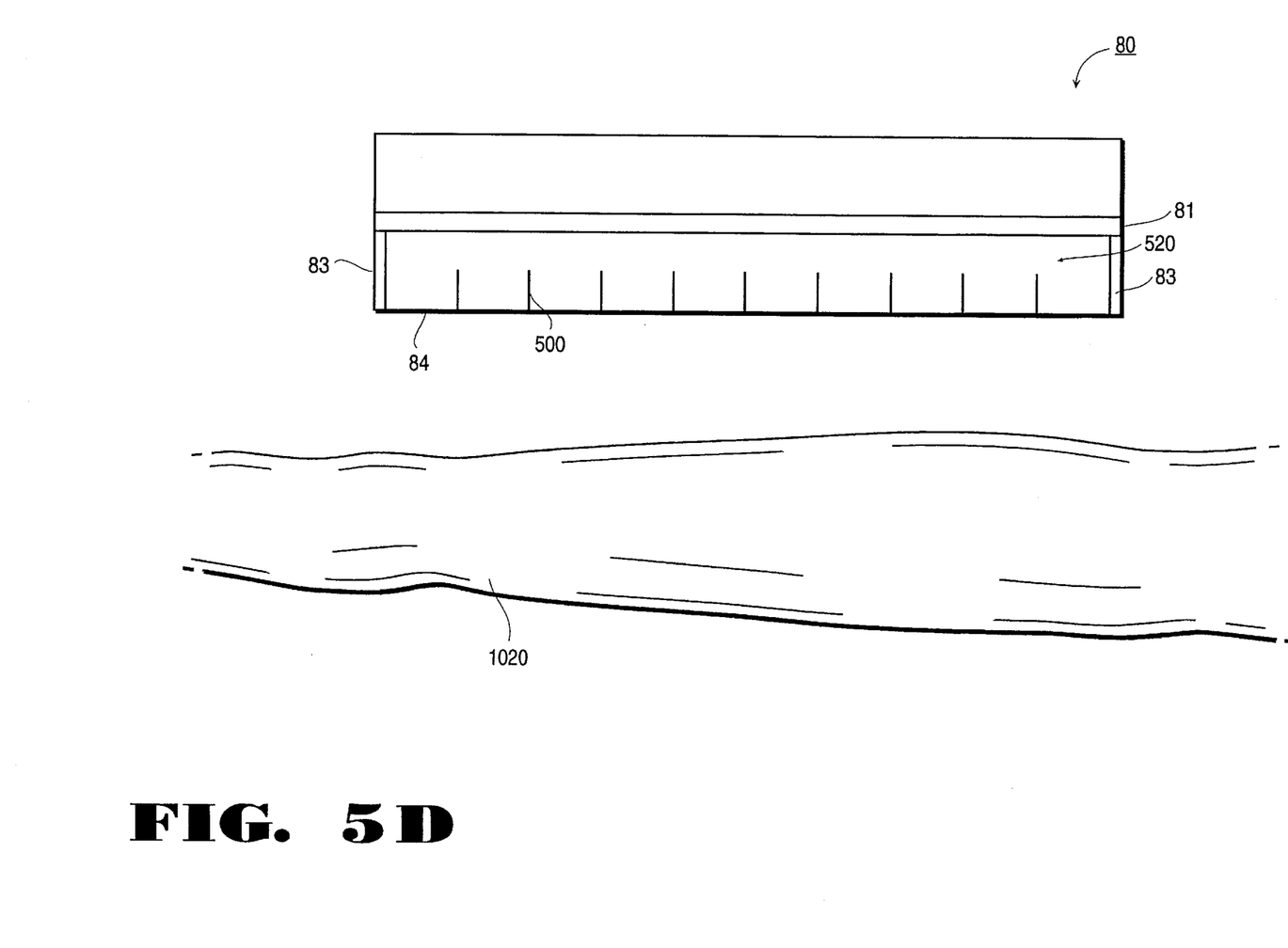
FIG. 5D illustrates detectors with a plate transparent to gamma rays.

The detector 80 has a thick frame 83 on its outer edge in order to protect the unusable part of the camera. The frame 83 is 2 inches high and one inch thick. As shown in FIG. 5D, a plate 84 transparent to gamma rays may be placed between the layer of septa 500 and the object 1020.

Figure 5E:
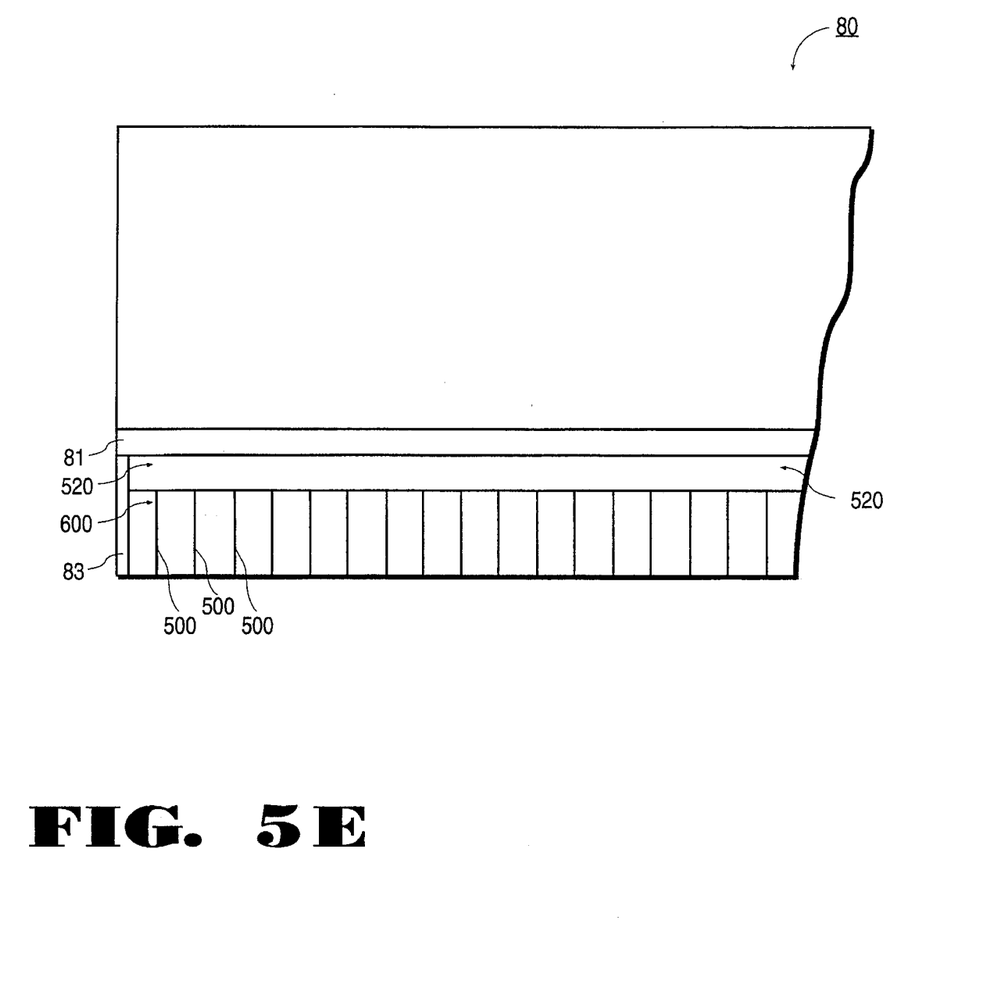
FIG. 5E illustrates a portion of a detector with septa in a sandwich construction.
Figure 5F:
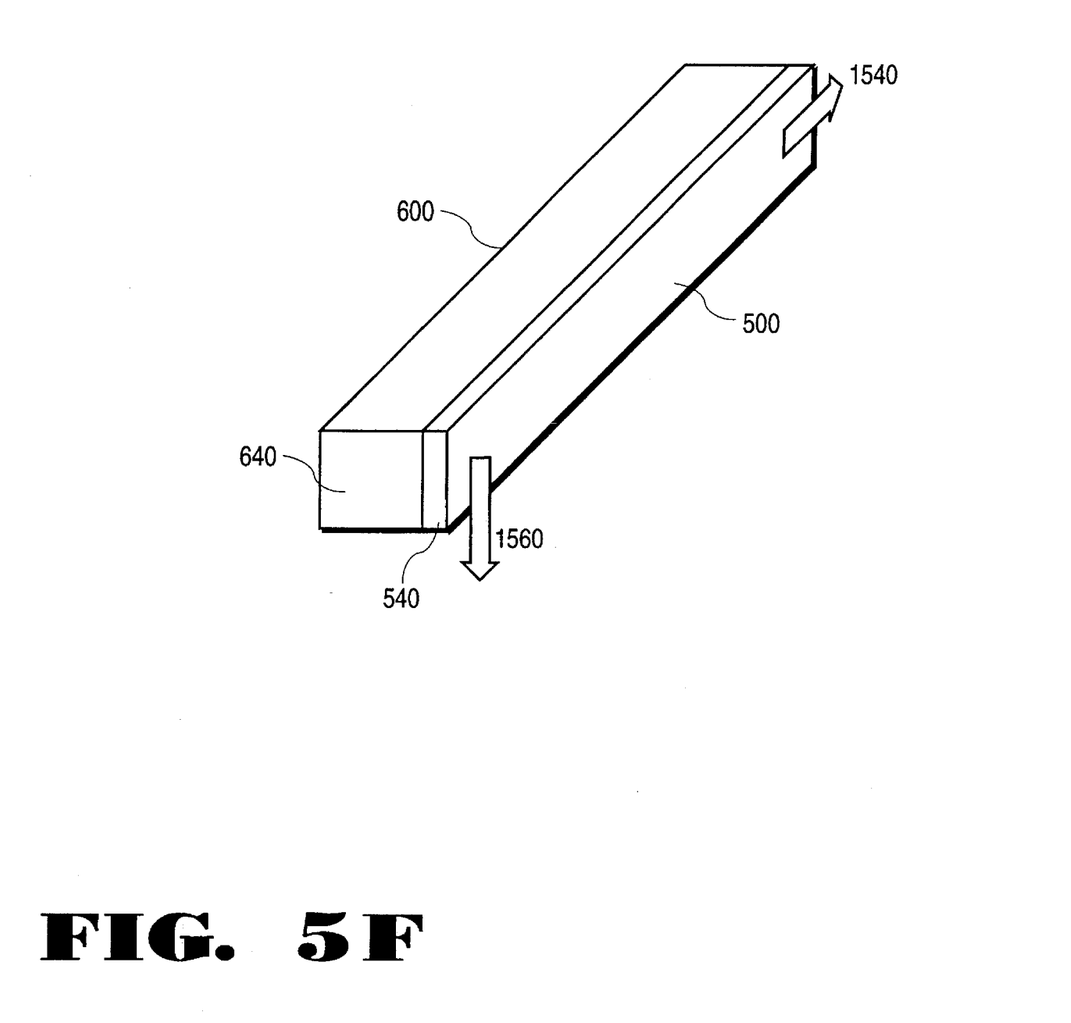
FIG. 5F illustrates a septum with a separator.

In another embodiment of the present invention, septa 500 are constructed from lead foil 500 and separated by foam or balsa wood separator material 600, as illustrated in FIG. 5E. This configuration is a "sandwich" construction. The separator material 600 allows radiation to pass while holding the thin septa 500 rigidly. FIG. 5F shows a single layer of the separator material 600 with a single septum 500. The thickness of cross-section 640 of the separator 600 is from 2 mm to 3.7 mm. The thickness of the cross section 540 of the lead foil 500 is 0.4 mm.

Figure 6A:
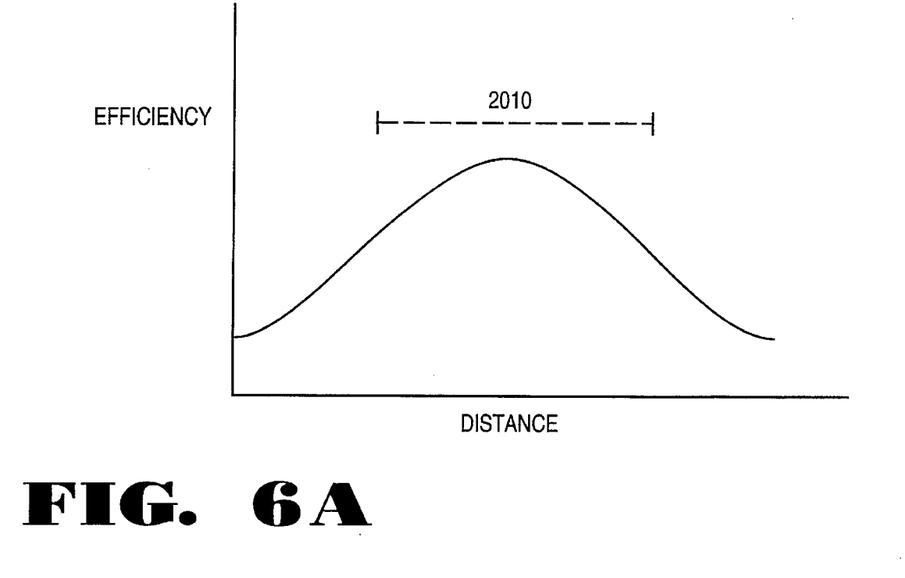
FIG. 6A illustrates radiation detection for a single detector.
Figure 6B:
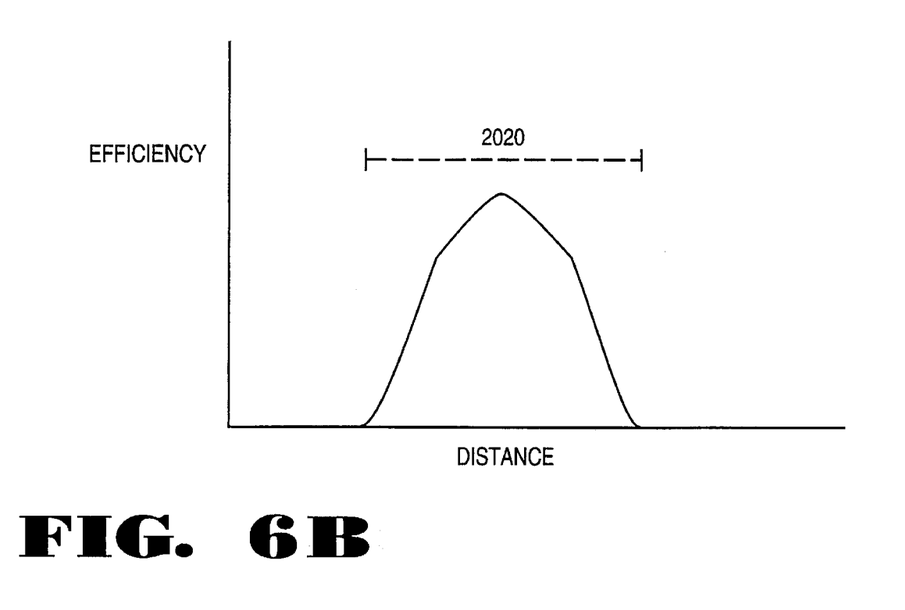
FIG. 6B illustrates radiation detection for a pair of detectors.

Referring to FIG. 6A, a single detector having septa 500 not extending to the imaging surface has the tendency to detect radiation in the field of view 2010. Similarly, in coincidence mode, radiation is detected in the field of view 2020, as illustrated in FIG. 6B. Because of the gap 520, some radiation is detected that would not be detected in a system having septa extending to the imaging surface.

Figure 7:
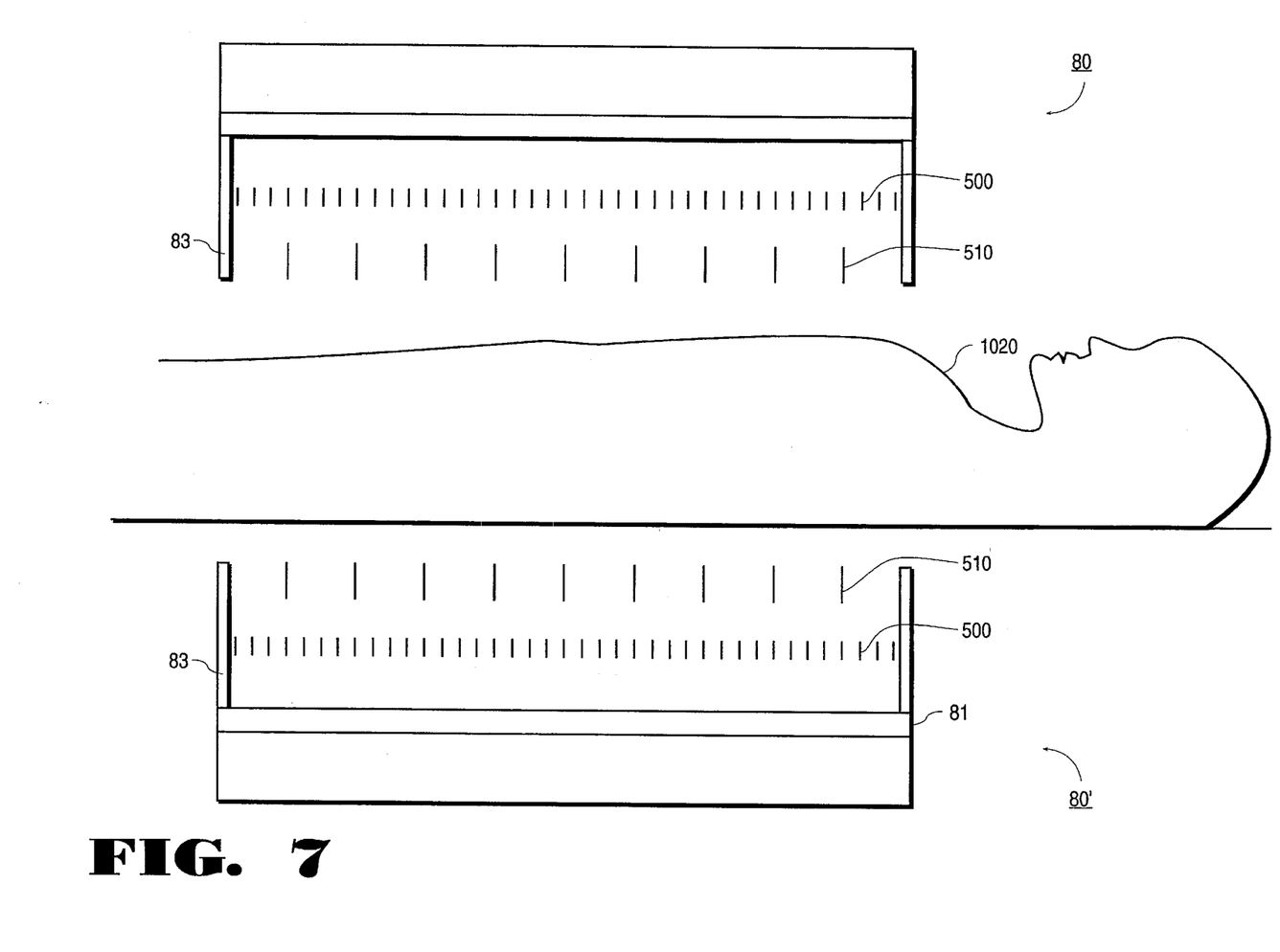
FIG. 7 illustrates detectors with two layers of septa.

A system may contain multiple layers of septa. In one embodiment, in addition to the first layer of septa 500, the system contains a second layer of septa 510 located between the first layer 500 and the patient 1020. FIG. 7 illustrates a system where each detector 80 and 80' has two layers of septa 500 and 510. There are gaps between the layers of septa. Although not shown, additional layers of septa could be added to make a total of three layers, four layers, and so on.

Figure 8A:
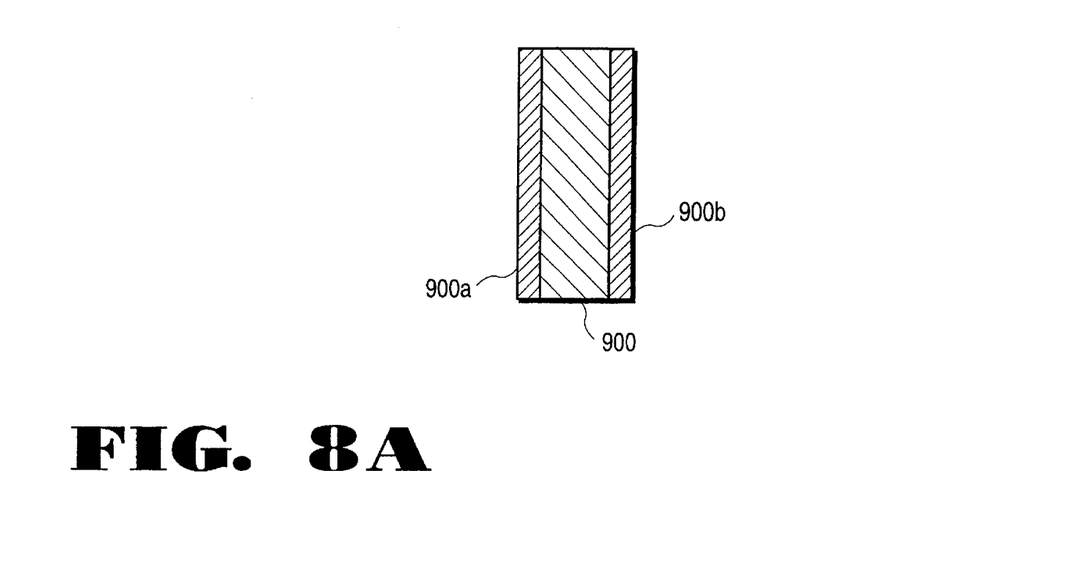
FIG. 8A illustrates a septum with a coating.

In order to block stray radiation while allowing non stray radiation to pass, in one embodiment a septum may be constructed with layers of different materials. As shown in FIG. 8A, the lead layer 900 of the septum is coated with copper layers 900a and 900b. This construction tends to block the weaker stray radiation while allowing the stronger non stray radiation to pass.

Figure 8B:
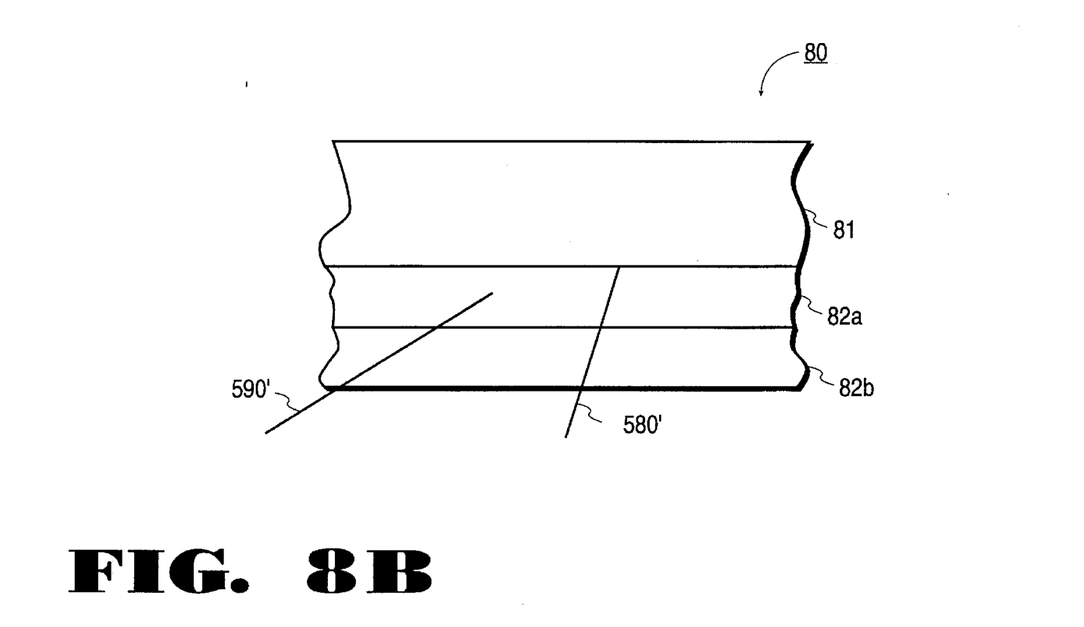
FIG. 8B illustrates the imaging surface with a graded absorber.

The imaging surface of the crystal 81 may be coated with a graded absorber in order to help reduce stray radiation while allowing non stray radiation to pass. FIG. 8B shows a portion of the imaging surface coated with a graded absorber. The absorber has a copper layer 82a on the imaging surface and a lead layer 82b on the copper layer 82a. The graded absorber blocks radiation having relatively low energy levels, such as radiation which results from scatter within the patient's body.

Figure 9:
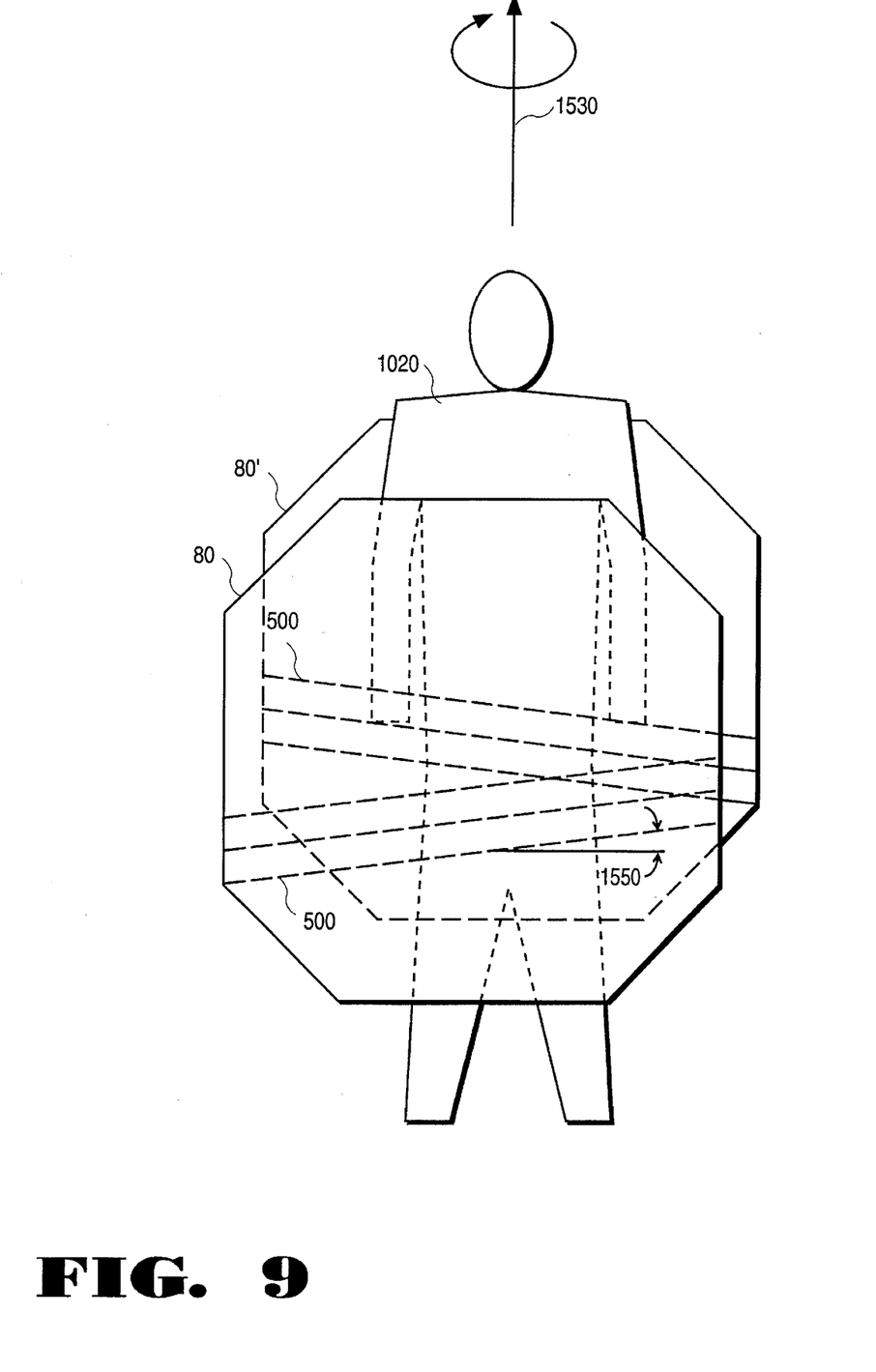
FIG. 9 is a transparent view of detectors with septa oriented at an angle from perpendicular to the axis of rotation of the detectors.

When septa 500 are oriented so that their long axis 1540 is perpendicular to the axis of rotation 1530 of the detectors, cold spots may be left on an image. These cold spots form because each septum stays within the same plane as it rotates about the patient 1020 with the detectors. In one embodiment, illustrated in FIG. 9, the septa do not stay within the same plane, because the long axis 1550 of each septum 500 is oriented at an acute angle 1550 away from perpendicular to the axis of rotation 1530, as illustrated in FIG. 9. FIG. 9 shows a top view of an embodiment of two detectors 80 and 80' with septa 500. With this configuration, the lines of the septa will appear to "walk" down different parts of the patient as the detectors 80 and 80' are rotated thus tending to average out the cold spots. Although the septa 500 are oriented at an angle 1550, the angle 1550 must not be too large so as to cause the septa 500 to no longer act as a stray radiation shield. Also, too large an angle may cause permanent dark spots in the image of a patient created during rotation.

Figure 10:
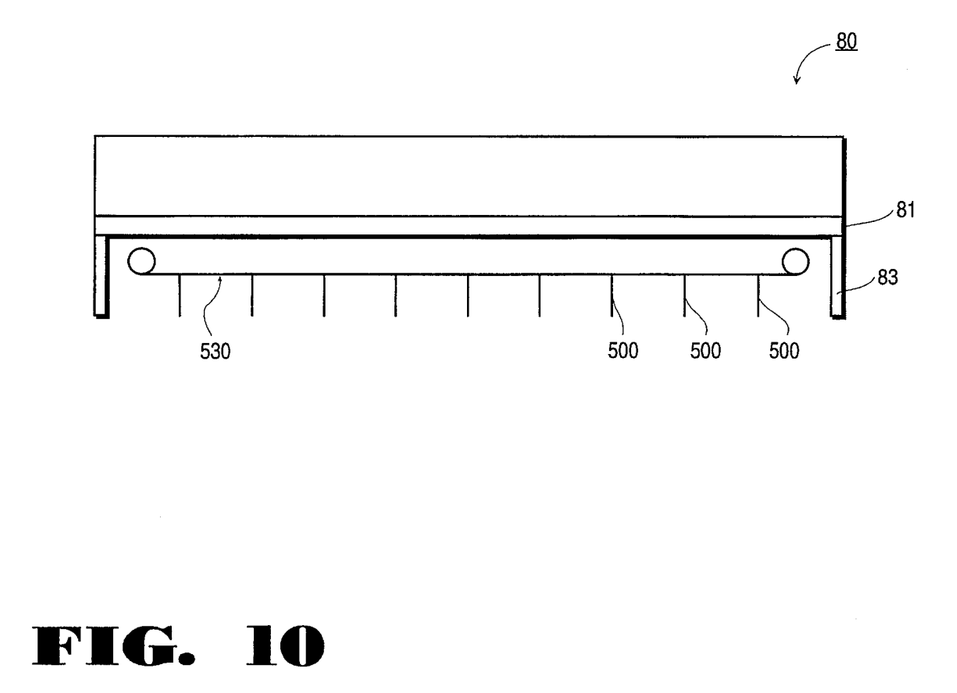
FIG. 10 illustrates a detector with moving septa.

Also to reduce cold spots on the image, the septa 500 may be moved in relation to the crystal 81 during the process of detection. As shown in FIG. 10, septa rest on a track 530 that can move the septa 500 in relation to the crystal 81. The track 530 would be constructed so as to allow radiation to pass through the track itself. It is envisioned that alternative apparatus could be used to move the septa in relation to the crystal 81.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A gamma camera for creating an image of an object, the gamma camera comprising:
   a detector having a scintillator, the scintillator having an imaging surface; and
   a first layer of septa disposed between the object and the imaging surface, the first layer including a plurality of individual septa disposed along the imaging surface, such that a gap exists between the imaging surface and the first layer of septa, wherein the gap has a size defined with respect to each of the individual septa, and wherein the size of the gap with respect to each of the septa depends upon the location of each of said septa relative to the imaging surface.

2. A gamma camera as described in claim 1 wherein the septa of the first layer are substantially rectangular and are spaced a predetermined distance from each other.

3. A gamma camera as described in claim 1 wherein the septa of the first layer are disposed parallel to each other.

4. A gamma camera as described in claim 1 wherein the septa are spaced by a separator material.

5. A gamma camera as described in claim 1 wherein the septa have a long axis disposed at an acute angle away from perpendicular to an axis of rotation of the detector.

6. A gamma camera as described in claim 1 wherein the septa comprise:
   a lead surface; and
   a copper coating disposed about the lead surface.

7. A gamma camera as described in claim 1 further comprising a second layer of septa including a plurality of individual septa, the second layer disposed between the object and the first layer of septa.

8. A gamma camera as described in claim 1 wherein the imaging surface is coated with a graded absorber.

9. A gamma camera as described in claim 1 further comprising means for moving the septa relative to the imaging surface.

10. A gamma camera as described in claim 1, wherein the individual septa have unequal widths.

11. A gamma camera system for creating an image of an object, the gamma camera system comprising a first detector and a second detector disposed opposite the first detector for coincidence detection, the first detector comprising:
    an imaging surface; and
    a first layer of septa including a plurality of individual septa, the first layer disposed between the object and the imaging surface, such that a gap exists between the imaging surface and the first layer of septa, wherein the septa have a long axis disposed at an acute angle away from perpendicular to an axis of rotation of the first detector and the second detector.

12. A gamma camera system as described in claim 11, wherein the individual septa have unequal widths.

13. A gamma camera system as described in claim 11, wherein the gap has a size defined with respect to each of the individual septa, and wherein the size of the gap with respect to each of the septa depends upon the location of each of said septa relative to the imaging surface.

14. A gamma camera system as described in claim 11 Wherein the septa of the first layer comprise:
    a lead surface; and
    a copper coating disposed about the lead surface.

15. A gamma camera system as described in claim 14 wherein the septa are substantially rectangular and are parallel spaced a predetermined distance from each other, and the septa further have a short axis disposed substantially perpendicular to the imaging surface.

16. A gamma camera system as described in claim 11 wherein the first detector further comprises a second layer of a plurality of septa disposed between the object and the first layer of septa.

17. A gamma camera system as described in claim 11 wherein the imaging surface is coated with a graded absorber.

18. A gamma camera system as described in claim 17 wherein the septa are substantially rectangular and are parallel spaced a predetermined distance from each other, and the septa further have a short axis disposed substantially perpendicular to the imaging surface.

19. A gamma camera system as described in claim 11 wherein the septa are spaced by a separator material.

20. A gamma camera system as described in claim 19 wherein the septa are substantially rectangular and are parallel spaced a predetermined distance from each other, and the septa further have a short axis disposed substantially perpendicular to the imaging surface.

21. A gamma camera system as described in claim 11 further comprising means for moving the septa relative to the imaging surface.

22. A gamma camera system as described in claim 21 wherein the means for moving the septa comprises a moveable track, wherein the septa are disposed upon the track.

23. A gamma camera system as described in claim 21 wherein the septa are substantially rectangular and are parallel spaced a predetermined distance from each other, and the septa further have a short axis disposed substantially perpendicular to the imaging surface.

24. A positron emission tomography (PET) system for generating images of an object, the PET system comprising:
    a gantry;
    a coincidence timing circuit;
    a first detector and a second detector coupled to the coincidence timing circuit for performing coincidence detection, the first detector and the second detector mounted on the gantry for rotation about an axis of rotation, the first detector comprising;
    a single, continuous scintillator having an imaging surface; and
    a first layer of a septa for blocking stray radiation from reaching the imaging surface, the first layer including a plurality of individual septa, the first layer disposed along the imaging surface between the object and the imaging surface, wherein the first detector has a gap between the imaging surface and the first layer of septa and wherein the gap has a variable size.

25. A positron emission tomography system as described in claim 24 wherein the septa are substantially rectangular and are parallel spaced a predetermined distance from each other, and the septa further have a short axis disposed substantially perpendicular to the imaging surface.

26. A positron emission tomography system as described in claim 24 wherein the long axes of the septa of the first layer are disposed at an acute angle away from perpendicular to the axis of rotation.

27. A positron emission tomography system as described in claim 26 wherein the septa of the first layer are substantially rectangular and are spaced a predetermined distance from each other and are parallel to each other, and the septa further have a short axis disposed substantially perpendicular to the imaging surface.

28. A positron emission tomography system as described in claim 24 wherein the septa of the first layer comprise:
   a lead surface; and
   a copper coating disposed about the lead surface.

29. A positron emission tomography system as described in claim 24 wherein the first detector further comprises a second layer of a plurality of septa disposed between the object and the first layer of septa.

30. A positron emission tomography system as described in claim 24 wherein the imaging surface is coated with a graded absorber.

31. A positron emission tomography system as described in claim 24 wherein the septa are mounted on a track for moving the septa relative to the imaging surface.

32. A positron emission tomography system as described in claim 24 wherein the septa have unequal widths.

33. A positron emmission tomography (PET) system for generating images of an object, the PET system comprising:
   a gantry;
   a coincidence timing circuit;
   a first detector and a second detector coupled to the coincidence timing circuit and mounted on the gantry for rotation about an axis of rotation, the first detector comprising:
      a scintillator having an imaging surface, said imaging surface coated with a graded absorber;
      a first and a second layer of septa including a plurality of parallel-disposed individual septa for blocking radiation, the second layer disposed between the first layer and the object, the first layer disposed between the object and the imaging surface such that a gap exists between the imaging surface of the first detector and the first layer of septa, the septa spaced a predetermined distance from each other, a short axis of the septa disposed substantially perpendicular to the imaging surface, and the septa disposed at an acute angle away from perpendicular to the axis of rotation, the septa comprising:
         a lead surface; and
         a copper coating disposed about the lead surface.

34. A gamma camera for creating an image of an object, the gamma camera comprising:
   a detector including a scintillator, the scintillator having an imaging surface; and
   a first layer of septa disposed between the object and the imaging surface, the first layer including a plurality of individual septa disposed along the imaging surface, wherein the septa have a long axis disposed at an acute angle away from perpendicular to an axis of rotation of the detector.

35. A gamma camera for creating an image of an object, the gamma camera comprising:
   a detector including a scintillator, the scintillator having an imaging surface; and
   a first layer of septa disposed between the object and the imaging surface, the first layer including a plurality of individual septa disposed along the imaging surface, such that a gap exists between the imaging surface and the first layer of septa, wherein the gap has a size defined with respect to each of the individual septa, and wherein the size of the gap with respect to each of the septa depends upon the location of each of said septa relative to the imaging surface.

36. A positron emission tomography (PET) system for generating images of an object, the PET system comprising:
   a gantry;
   a coincidence timing circuit;
   a first detector and a second detector coupled to the coincidence timing circuit for performing coincidence detection, the first detector and the second detector mounted on the gantry for rotation about an axis of rotation, the first detector including:
   a scintillation element having an imaging surface; and
   a first layer of a septa for blocking stray radiation from reaching the imaging surface, the first layer of septa including a plurality of individual septa, the first layer of septa disposed along the imaging surface between the object and the imaging surface; and
   a second layer of septa disposed between the object and the first layer of septa.

* * * * *